(12) United States Patent
Andrysek et al.

(10) Patent No.: US 6,403,122 B1
(45) Date of Patent: *Jun. 11, 2002

(54) IMMUNOMODULATORY PHARMACEUTICAL COMPOSITION ADOPTED TO FORM LYOTROPHIC LIQUID CRYSTALS IN CONTACT WITH AN AQUEOUS PHASE

(75) Inventors: Tomas Andrysek; Milan Stuchlik, both of Opava; Vladimir Matha; Alexander Jegorov, both of Ceske Budejovice; Ales Husek, Opava; Josef Stuchlik, Hrabyne, all of (CZ)

(73) Assignee: Galena AS, Opava (CZ)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/927,992

(22) Filed: Sep. 12, 1997

(30) Foreign Application Priority Data

Sep. 12, 1996 (CZ) .................................. 2677/96

(51) Int. Cl.⁷ .......................... A61K 9/10; A61K 9/48; A61P 31/00
(52) U.S. Cl. .................. 424/484; 424/400; 424/455
(58) Field of Search ................. 424/488, 400, 424/484, 455; 514/975, 946, 944

(56) References Cited

FOREIGN PATENT DOCUMENTS

| DE | 3915617 A | 11/1989 |
|---|---|---|
| GB | 2218334 A | 11/1989 |
| WO | WO 95/25504 | 9/1995 |
| WO | WO 96/13249 | 5/1996 |
| WO | WO 97/26003 | 7/1997 |

*Primary Examiner*—Edward J. Werman
(74) *Attorney, Agent, or Firm*—Beyer Weaver & Thomas LLP (57) ABSTRACT

Pharmaceutical compositions especially for internal application which create lyotropic liquid crystals when in contact with aqueous phase. The pharmaceutical compositions consist of:

A hydrophobic active ingredient with immunomodulatory effect from a group of N-methylated cyclic undecapeptides or macrolide antibiotics, in quantity 1–35 weight % in a carrier medium containing B at least one absorption promoter allowing for contact of the drug with a biological membrane or passing of the drug through in quantity 1–40 weight %, C nonlipidic vehicle containing at lest one of the below mentioned substances:
C1 surfactant or mixed surfactant with HLB>9, in quantity 1–80 weight %
C2 lipophilic solvent from group of higher fatty alcohols in quantity 1–30 weight %
C3 at least one cosurfactant in quantity 1–50 weight %, while a ratio among the individual components of the product is A:B:C=1:0.5–4:5–8.

12 Claims, 4 Drawing Sheets

IMMUNOMODULATORY PHARMACEUTICAL COMPOSITION ADOPTED TO FORM LYOTROPHIC LIQUID CRYSTALS IN CONTACT WITH AN AQUEOUS PHASE

FIELD OF THE INVENTION

This invention relates to a pharmaceutical immunomodulatory formulation particularly but not exclusively comprising a cyclosporin as active ingredient. The invention relates to formulations for internal use and also to topical formulations.

DETAILED DESCRIPTION OF PREFERRED EMBODIMENTS

Cyclosporins are immunosuppressive cyclic undecapeptides which are used particularly in relation to organ transplants. Cyclosporins are also used for treatment of autoimmune diseases and inflammatory conditions such as arthritis and rheumatic diseases. Further applications include antiparasitic treatments and cancer therapy. Certain cyclosporins which are devoid of immunosuppressive activity have been found to exhibit an inhibitory effect towards replication of the HIV-1 virus and these compounds can be employed in therapy for treatment and prevention of AIDS or AIDS related diseases.

A wide variety of cyclosporins has been identified. Cyclosporins are highly hydrophobic and are consequently difficult to formulate in dosage forms providing adequate bioavailability. Solubility of cyclosporins in water typically does not exceed 25 mg/l. The high lipophilicity of cyclosporins is indicated by the value of the partition coefficient P in the system n-octanol/water. For cyclosporin, values of log P=2.08 to 2.99 have been reported.

Mixed natural vegetable or animal oils specifically purified or interesterified triacylglycerols of medium or long chain fatty acids commercially available under the trade names Miglyol®, Captex®, Myritol®, Capmul®, Neobene® and Mazol® are frequently used as lipophilic carriers. Mixtures of mono-, di- and triacyl glycerols are also used. As lipids are not capable of transport through the enteric epithelium membrane, they must undergo a degradation process within the gastrointestinal tract. Lipids which have been digested by lipolytic enzymes are absorbed in the upper part of the small intestine. These enzymes attack ester bonds of triacyl glycerols especially in the one and three positions to form 2-monoacylglycerol and the relevant fatty acid. These products are capable of transport through cell membranes and become a substrate for triacylglycerol resynthesis in the endoplasmatic reticulum. Transport through the membrane is possible only if the hydrophilic barrier caused by the immiscible aqueous layer adjacent the enteric epithelium is overcome. To surmount this barrier the lipophilic substances must be in the form of a micellar solution.

As both fatty acids and monoacylglycerols are water soluble they must be dispersed in the enteric lumen by surface active substances. Bile acids create mixed micelles of approximately 40 to 80 nm with monoacylglycerols, fatty acids and cholesterol but cannot disperse triacylglycerols. However more than 50% of dietetically ingested triacylglycerols can be absorbed without bile acids. It has been observed that lamellar species, structurally corresponding to liquid crystals are separated from roughly dispersed lipids in the enteric lumen. This transient phase spontaneously dissolves in the presence of an adequate quantity of bile acids and releases the lipophilic phase into micelles. It is likely that transport from mixed micelles remains the major route of lipid reabsorption in healthy people.

Triacylglycerols, mixtures of mono-, di and triacylglycerols or mixtures of mono- and diacylglycerols are not ideal carriers for lipophilic pharmaceutical compositions because the lipolytic degradation process is influenced by a number of factors, for example pH, the presence of colipases, bile acids and bicarbonate in the enteric lumen. However several commercially available formulations use such systems, for example as sold under the trade names Consupren®, Sandimmun®, Implanta® and Neoral®. Triacylglycerol systems are also disclosed in GB-A-2222770, WO94/05312 and EP-A-650721. A combination of interesterified triacylglycerol with surfactant of low HLB value is disclosed in WO94/08603 and WO94/08605. A triacylglycerol carrier extended by partial esters of fatty acids with glycerol or sorbitol is disclosed in GB-A-2228198.

Use of a product of glycerol transesterification with polyethoxylated vegetable oil and use of mixed mono-, di- and triacylglycerols as lipophilic carriers is disclosed in GB-A-2270842. The substances are commercially available under the Labrafil® trade mark.

To overcome the necessity of lipolysis before absorption, liquid crystal formation was disclosed in EP-A-0314689 and EP-A-0126751. Apart from potential stability problems, the correct bioavailability for the active ingredient was difficult to achieve. The suitability of these controlled-release system for poorly absorbable drugs, such as cyclosporin, is brought into question by the narrow absorption window. The composition disclosed in EP-A-0314689 contains triacylglycerols.

The object of the present invention is a pharmaceutical composition with high bioavailability based on a lipolytic indifferent vehicle, an absorption promoter and the active ingredient, which after application into the gastrointestinal tract creates a liquid crystal mesophase and further dissolves to form a very fine suspension. Pharmaceutical compositions in accordance with this invention may create a priori an easily absorbed substrate that potentially enables very high bioavailability of the drug even in the event of lipolytic or biliar insufficiency (eg at Zollinger-Ellison syndrome). Preferred formulations simultaneously create a transient liquid crystal phase upon application into an aqueous medium, allowing a parallel route of lipid absorption from the enteric lumen in addition to the known absorption from mixed micelles.

According to the present invention an immunomodulatory pharmaceutical composition adopted to form lyotropic liquid crystals in contact with an aqueous phase comprises:

A) 1 to 35% by weight of an active ingredient selected from: N-methylated cyclic undecapeptides or macrolide lactones; and a carrier medium comprising:

B) 1 to 40% by weight of at least one absorption promoter;

C) a non-lipidic vehicle containing at least one of:
   (i) 1 to 80% by weight of a surfactant or mixtures of surfactant with an HLB greater than 9:
   (ii) 1 to 30% by weight of a lipophilic solvent comprising one or more higher fatty alcohols; and
   (iii) 1 to 50% by weight of at least one surfactant;
wherein the ratio of components A:B:C is 1:01–20; 0.5–35 by weight and wherein the aforementioned amounts of ingredients total 100%.

References to liquid crystals in the specification denote an intermediate state between solid crystals and isotropic liquids characterised by long range order and short range properties close to those of a simple liquid or solution. Liquid crystalline phases obtained from compositions of this invention are thermodynamically stable, viscous and optically isotropic phases comprising the amphiphilic formulation and water.

Component A may include a cyclosporin as active ingredient, for example one or more cyclosporins selected from immunosuppressively active cyclosporin, [Nva]$^2$-cyclosporin, [MeIle]$^4$-cyclosporin and [3-0-acylMeBmt]$^1$-cyclosporin.

Alternatively Component A may comprise immunomodulatory acting substances selected from the group of macrolidic lactones produced by bacteria of the genus Streptomyces or their derivatives, advantageously rapamycine or tacrolimus.

Component B may be selected from:

B1 saturated or unsaturated $C_{R-22}$ fatty acids preferably with a melting point lower than 25° C. or mixtures thereof; or B2 polar pseudolipids selected from polyglycerol esters of fatty acids of general formula:

(1)

where n is an integer from 0 to 14 and R=H or acyl group derived from $C_{8-22}$ saturated and/or unsaturated fatty acids and/or hydroxy fatty acids or mixtures thereof or B3 glycerol monoesters with high fatty acids;

or a suitable combination of components in B1, B2 and B3;

wherein the ratio B:A is 0.5:1 to 6:1.

Component C comprises a non-lipidic vehicle containing at least one of the compounds mentioned below:

C1 a surfactant of mixture of surfactants with HLB>9, in a quantity 1–80 weight %

C2 unsaturated $C_{12}$ to $C_{22}$ fatty alcohols; the ratio between components C2 and C1 being preferably from 0 1:1 to 4.5:1

C3 at least one surfactant preferably selected from the compounds mentioned below in an amount from 1 to 50 weight %.

Preferred compositions include a combination of components C2 and C1 in a ratio C2:C1 of 0.1:1 to 4.5:1.

C3 component is advantageously selected from:

C3.1 polyether of general formula H—[O—CH$_2$—CH$_2$—]$_n$—OH, wherein n is an integer from 2 to 20;

C3.2 cyclic polyether of general formula (2)

(2)

C3.3 A substance selected from polyols especially with three C—atoms and/or their mono- to poly- esters with sorbitans of fatty acids, macrogolsorbitans of fatty acids, polyoxyethylated fatty acids or mono- to polyesters of fatty acids;

wherein the total quantity of Component C3 is between 5–30 weight %.

Formulations in accordance with this invention may contain at least one component D which serves to adjust the appearance, taste, stability against microbial contamination and autooxidative processes or change the product into a form of lyotropic crystals during preparation. The ratio of components D:(A+B+C) may be 0.01 to 10:1, advantageously 0.1 to 6:1.

Formulations in accordance with the present invention confer a number of advantages. Addition of an aqueous phase to a preferred composition provides a gel-like composition. Preparation of topical gel dosage forms is facilitated, allowing such a gel to be prepared immediately before use in the required quantity. The absence of commonly used low boiling hydrophilic solvents is avoided. Such solvents complicate production of dosage forms such as capsules due to solvent migration into and through the capsule shell wall.

Alternative embodiments of the invention afford a self assembly drug delivery system (SADDS). A self assembly drug delivery system may be considered to be a pharmaceutical composition which is a liquid, semi solid or solid at room temperature with a homogeneously dispersed substance, preferably in the form of a genuine solution which spontaneously forms a self-associating dispersion based mostly on liquid crystals when in contact with an aqueous phase. By aqueous phase we mean water, physiological fluids for example gastric fluid, enteric fluid, tears, blood, electrolyte solutions etc and glycerol. SADDS can initially contain a certain quantity of aqueous phase in a quantity between about 0.5 and 80% by weight of the product. The size of the particles resulting from complete dispersion of the product in an aqueous phase advantageously ranges to a maximum of 1000 nm. Such a dispersion is substantially or completely transparent and may be slightly blue to intensively milky in appearance according to the character and size of the particles. The size distribution of the dispersed particles does not have to exhibit a single maximum. Pharmaceutical compositions of this invention may exhibit a distribution of particles into various size categories.

Generally SADDS consist of a mixture of oils or oily phase an non-ionic surfactant. Furthermore such a system may contain other auxiliary substances for increasing drug dissolution or adjusting surface tension of physical, microbial or organoleptic properties of the formulation.

These systems may also be characterised by creation of a gel-like mesophase when in contact with water or aqueous medium. Formation of such phase is possible both in vitro, by addition of aqueous medium in a ratio of approx. 1:6 (self-dispersed system : aqueous medium) and in vivo, by application into the gastrointestinal tract, conjunctival sac or mucosa. This mesophase has a lyotropic liquid crystal character. Further dispersion results in formation of a monogenous dispersion whose type depends on the polarity of the system and the value of the hydrophilic/lipophilic balance. The rate of formation of the homogenous dispersion depends on the viscosity and proportion of hydrophilic components in the vehicle at constant dispersion conditions and can be influenced by both selection of a suitable ratio between the lipophilic solvent and surfactant and by selection of a suitable cosurfactant. These properties allow for various modifications of a system and objective distribution of a drug in the gastrointestinal tract.

The pharmaceutical composition prepared in this way may be dispersed in aqueous medium first in a semisolid form or a gel like mesophase, that is subsequent dissolved to form required type of dispersion.

Generally a mesophase of this type is created by mild interactions of polar lipids with an aqueous medium and may be described as "lyotropic liquid crystal" thanks to its ordered molecular structure. According to nature the molecular association, we classify lamellar $L_\alpha$-phase, cubic C-phase, hexagonal $H_1$-phase (normal) and $H_2$-phase (inverse), micellar $L_1$-phase and $L_2$-phase (inverse). The general techniques for classification of individual mesophases include: X-ray diffraction, volumetric changes, rheology, nmr, calorimetry and microscopy in polarised light.

Although the substances defined in paragraph C2 do not belong to a group of polar lipids as they are non-polar fatty alcohols, they can be advantageously used in combination with C1 substances in ratio between 0.1:1 to 4.5:1. When in contact with aqueous medium, this mixture may form $L_\alpha$, $H_1$, $L_1$, $H_2$ or $H_2$ mesophases. The type of the resulting mesophase depends on quantity of aqueous medium which penetrates into or is deliberately added to the system or can be modified by the C2 component. A suitable combination of the substances defined in paragraph B and C causes the system to spontaneously create a required type of mesophase, preferably lamellar or hexamogonal if there is an excessive amount of aqueous medium.

As a component A one can use hydrophobic active ingredients having immunomodulatory effect selected from the group of N-methylated cyclic undecapeptides or macrolidic antibiotics. It is advantageous to use immunosuppressively active cyclosporins especially cyclosporin (also known as Cyclosporin A), [Nva]$^2$-cyclosporin (cyclosporin G), [Melle]$^4$-cyclospirin and [3-O-acyl MeBmt]$^1$-cyclosporin. As a component A we can also use active ingredients from group of macrolidic peptides or lactones produced especially by gram-positive Streptomyces, advantageously by Streptomyces hygroscopicus which produce rapamycine or by Streptomyces tsukubaensis which produce tacrolimus. Pharmaceutical compositions of this invention may contain 1 to 35.0 weight % of the active ingredient.

As component B1 one can use compounds selected from $C_{8-22}$ saturated or unsaturated fatty acids, advantageously those whose melting point is lower than 25° C., for example caprylic, palmitoleic, oleic, gadoleic, gadoelaidic, linoleic, linolenic, arachidonic and docosahexanoic acids.

As the human organism is unable to synthesise unsaturated fatty acids with more than 9 carbons and it, fully dependent on their external intake, these acids may be used with advantage in formulations according to this invention. Commercially available mixtures of fatty acids such as Edenor® SB 05 or Emery® 644 (Henkel) are also suitable for purposes of the pharmaceutical compositions according to this invention.

As component B2 polyglycerol esters with middle and long chain fatty acids of the formula (3) can be advantageously used. Its general structural formula is as follows:

(3)

wherein n is an integer from 0 to 14 and R=H or $C_{8-22}$ acyl derivative of saturated, unsaturated or hydroxy fatty acids.

Generally, polyglycerol esters with fatty acids are prepared by either partial esterification of polyglycerols with the corresponding fatty acids or transesterification of vegetable oil with polyglycerol. Each individual polyglycerol ester may be characterised by the saponification number. Hydroxyl number is best indicated by the polymerisation level. Among others, the following polyglycerol esters are suitable for preferred formulations according to this invention.

| | |
|---|---|
| Diglycerylmonooleate | DGMO-C, DGMO-90 |
| Hexaglycerylmonooleate | NIKKOL HEXAGLYN 1-0 |
| Hexaglyceryldioleate | Plurol oleique WL 1173 |
| Octaglycerylmonostearate | SANTONE 8-1-S |
| Octaglycerylmonoleate | SANTONE 8-1-O |
| Decaclycerylmonolaurate | NIKKOL DECAGLYN 1-L |
| Decaglycerylmonomyristate | NIKKOL DECAGLYN 1-M |
| Decaglycerylmonostearate | NIKKOL DECAGLYN 1-S |
| Decaglycerylmonooleate | NIKKOL DECAGLYN 1-O |

NIKKOL is a trade mark of Nikko Chemicals Co under NIKKOL®, SANTONE® is a trade mark of Durkee Foods Co, and Plurol oleique is a trade mark of Gattefosse Co.

Preferred polyglycerol esters used in the formulation of this invention are characterised by the following purity tests:

Acid number—max 6, content of heavy metals—max 10 ppm, water content—max 2%, content of Na salts of fatty acids—max 2% (as Na stearate), total ash—max 1%.

Monoacylglycerols of Component B3 may have a monoester content of at least 90%. Products with the following ranges of physico—chemical characteristics produced by Grinsted Co are suitable:

| composition of fatty acids | GMO | GMO 90 |
|---|---|---|
| oleic acid | min 78% | min 92% |
| linoleic and linolenic acid | max 15% | — |
| linolenic acid | — | max 6% |
| saturated acids $C_{16}$, $C_{18}$, $C_{20}$ | max 10% | — |
| saturated acids $C_{16}$, $C_{18}$ | — | max 2% |
| content of free fatty acids | max 1.5% | max 0.5% |

Similar products of Eastman Co produced under trade name Myverol 18-99 (glycerylmonoleate) or Myverol 18-92 (glycerylmonolinoleate) with minimum content of 90% monoesters can be employed.

Glycerylmonoesters with shorter alkyl chains about $C_8$ to $C_{10}$, such as glycerylmonooctanoate or glycerylmonodecanoate produced by Larodan Fine Chemicals Co (Sweden) or The Nishim Oil Mills Ltd (Japan) can also be employed.

Suitable combination of the above mentioned absorption promoters may be used to achieve desired blood levels of the hydrophobic active ingredient.

The surfactant or mixture thereof of compound C1 provides a hydrophilic-lipophilic balance (HLB) higher than 9, or by a mixture of surfactants whose resulting HLB has this value. As HLB value is of additive character, it is possible to calculate HLB value of mixed surfactant according to the following formula based on known HLB values of original surfactants and percentage abundance of the individual surface-active components.

$$HLB_C = \frac{HLB_A \cdot X_A + HLB_B \cdot X_B}{(X_A + X_B)}$$

where $HLB_C$=HLB value of mixed surfactant

$HLB_A$=HLB value of A surfactant $HLB_B$=HLB value of B surfactant

$X_A$=portion of A surfactant in mixed surfactant $X_B$=portion of B surfactant in mixed surfactant For instance, surface-active compounds characterised as esters of $C_{8-22}$ fatty acids unhydrogenated or hydrogenated with macrogolglycerols may be used. According to this invention, one can advantageously use macrogolglycerols with castor oil of general formula (4)

or macrogolglycerols with hydrogenated castor oil of general formula (5)

The following substances characterised by a number of reacted ethyleneoxide mols (1+m+n+x+y+z) and HLB value are particularly advantageous.

|  | (1 + m + n + x + y + z) | HLB |
|---|---|---|
| macrogol(1540) glyceroltriricinoleate | 35 | 12–14 |
| macrogol(1760) glycerolhydroxystearate | 40 | 12.5–16 |
| macrogol(2200) glycerolhydroxystearate | 50 | 13.5 |
| macrogol(2640) glycerolhydroxystearate | 60 | 14.5 |
| macrogol(3520) glycerolhydroxystearate | 80 | 15 |
| macrogol(4400) glycerolhydroxystearate | 100 | 16.5 |

Characteristic physicochemical parameters for the mentioned substances are as follows:

Acid number≦2; hydroxyl number=40–60; iodine number<1*; saponification number=40–70; water content<3%.

(*- for macrogol(1540) glyceroltriricinoleate=28–32).

These substances are commercially available under various trade marks eg Cremophor®, Nikkol®, Simulsol® and Mapeg®. They are commonly used for their solubilization properties in topical, oral and intravenous products.

Mixed mono- and di- macrogolesters of mono-, di- and triaclglycerol may be employed for example as commercially available under Gelucir® trade mark preferably Gelucir® 50/13 and 44/14.

The percentage abundance of acyls of fatty acids is as follows:

|  | Abundance/% | |
|---|---|---|
| Gelucire ® | 50/13 | 44/14 |
| $C_8$ caprate | <3 | 10 |
| $C_{10}$ caprinate | <3 | 9 |
| $C_{12}$ laurate | <5 | 50 |
| $C_{14}$ myristate | <5 | 24 |
| $C_{16}$ palmitate | 50 | 14 |
| $C_{18}$ stearate | 58 | 15 |

Physicochemical properties are as follows:

Acid number<2,00; saponification number+65–95; iodine number<2; hydroxyl number+36–56; peroxide number<6; alkaline impurities<80 ppm; aqueous glycerol content<3.00%

Macrogol (352) glycerolcaprilocaprinate is another preferred substance and may be characterised by the following physicochemical properties:

HLB=14; number of ethylene oxide mols-8; acid number<1,00; saponification number+85–105; iodine number<2; peroxide number<12.5; free glycerol content<5.0.

It is commercially available under the Labrasol® trade mark.

Macrogolesters of fatty acids, eg marogol(660)-12-hydroxystearate characterised by the following physicochemical parameters are preferred for component C1. The physicochemical properties are: Acid number<1; water content<0.5%; saponification number+53–63; hydroxyl number=90–110. The compound is commercially available under the Solutol® trade mark.

Esters of pyrrolidone carboxylic acid with macrogolglycerol fatty acid esters available under the Pyroter® trade mark are also suitable. Advantageously, the compounds known as Pyroter GPI 25 and Pyroter CPI-40, characterised by the following parameters can be used.

|  | GPI-25 | CPI-40 |
|---|---|---|
| HLB | 13.4 | 9.3 |
| number of ethylenoxide mols | 25 | 20 |
| acid number | <3 | <13 |
| saponification number | 67–83 | 89–105 |
| water content | <0.3% | <0.3% |
| density | 1080–1110 | 1025–1055 |

Poloxamer polyols can be used as the C1 component. These are block co-polymers of ethylene oxide and propylene oxide of general formula (6)

$$HO(C_2H_4O)_a(C_3H_6O)_b(C_2H_4O)_aH \quad (6)$$

where the values of "a" and "b" are as follows:

|  | a | b |
|---|---|---|
| poloxamer 124 | 12 | 20 |
| poloxamer 158 | 80 | 27 |
| poloxamer 237 | 64 | 37 |
| poloxamer 338 | 141 | 44 |
| poloxamer 407 | 101 | 56 |

The pysicochemical properties are as follows:

| poloxamer | Mr | ethylenoxide (%) | pH (2.5% solution) | heavy metals (%) | aqueous ethylenoxide, propylenoxide and 1,4-dioxan |
|---|---|---|---|---|---|
| 124 | 2090–2360 | 46.7 ± 1.9 | 5.0–7.5 | ≦0.002 | ≦5 ppm |
| 188 | 7680–9510 | 81.8 ± 1.9 | 5.0–7.5 | ≦0.002 | ≦5 ppm |
| 237 | 6840–8830 | 72.4 ± 1.9 | 5.0–7.5 | –≦0.002 | ≦5 ppm |
| 338 | 12700–17400 | — | 5.0–7.5 | ≦0.002 | ≦5 ppm |
| 407 | 9840–14600 | 73.2 ± 1.7 | 5.0–7.5 | ≦0.002 | ≦5 ppm |

$C_{8-22}$ unsaturated fatty alcohols can be used as the C2 component. Advantageously, one can use oleylalcohol (9-ocadecen-1 ol)

Polyethers of formula $H-[O-CH_2-CH_2-]_n-OH$, where n is a an integer from 2–140, advantageously n=2–20 may be used for component C3.1. Liquid or semisolid polyethylene glycols with average molecular weight 200–600 are preferred.

Suitable polyethylene glycols, which can be used have the following physicochemical properties:

|  | hydroxyl number | density g.cm$^{-3}$ | viscosity mPa.s | freezing point °C. |
|---|---|---|---|---|
| PEG 200 | 534–591 | 1.124 | 60–70 | –50 |
| PEG 300 | 356–394 | 1.125 | 85–100 | –15–10 |
| PEG 400 | 267–295 | 1.126 | 110–125 | 4–8 |
| PEG 600 | 178–197 | 1.126 | 16–19* | 17–22 |

*50% aqueous solution

Cyclic polyethers obtained by alkoxylation of anhydro derivatives of alcoholic hexoses such as sorbitol, mannitol and iditol may be used as the C3.2 component, for example isosorbide, isoidide and isomannide.

Suitable 2,5-di-O-methylderivatives result from the subsequent reaction with eg methyl chloride. Particularly suitable, is 2,5-dimethyl isosorbide produced under APLASOLVE® DMI trade mark (ICI Co) with the following physicochemical properties: Boiling point approx 234° C.; density $_{25°\ C.}$=1,164 g.cm$_{-3,}$ refractive index $_{25°\ C.}$=1,462; viscosity $_{25°\ C.}$=approx 5 mPa.s; dielectric constant $_{25°\ C.}$=cca 7; Hildebrand's solubility parameter=10,1 cal.cm$^{-3/2}$ The preferred C3.3 components are 1,2-propandiol and 1,2,3-propantriol. We can also use compounds characterised as esters of $C_{8-22}$ fatty acids or hydrogenated acids with macrogolsorbitans, advantageously compounds available under Tween® (ICI) and Montanox® trade marks (Seppic). Particularly suitable compounds include: polyoxyethylene (20)-sorbitan monoleate (Sween 80), polyoxyethylene (20)-sorbitan monostearate (Tween 60), polyoxyethylene (20)-sorbitan monopalmitate (Tween 40) and polyoxyethylene (20)-sorbitan monoleate (Tween 20).

Compounds of component C3 may participate in adjustment of physical properties of the formulation, especially when the formulation is in contact with aqueous medium in the gastrointestinal tract or when the concentrate is diluted prior to administration.

As far as combination of absorption promoter and non-lipidic vehicle product has a predictable degree of dispersion after application into GI tract, one can achieve a required bioavailability of the active ingredient with a well-balanced pharmaceutical composition even if one uses hydrophilic surfactants. For SADDS a large amount of such surfactant is necessary, but such compounds can cause lipolysis inhibition According to this invention we are able to prevent these problems with lipolysis by using non-lipidic vehicle. But, as can be seen from Example XI and FIG. 2 the formulation based on a non-lipidic vehicle is not sufficient to achieve desired blood levels and so use of the absorption promoters may be necessary.

The invention is further described by means of example but not in any limitative sense with reference to FIGS. 1 to 4.

Figure 1:
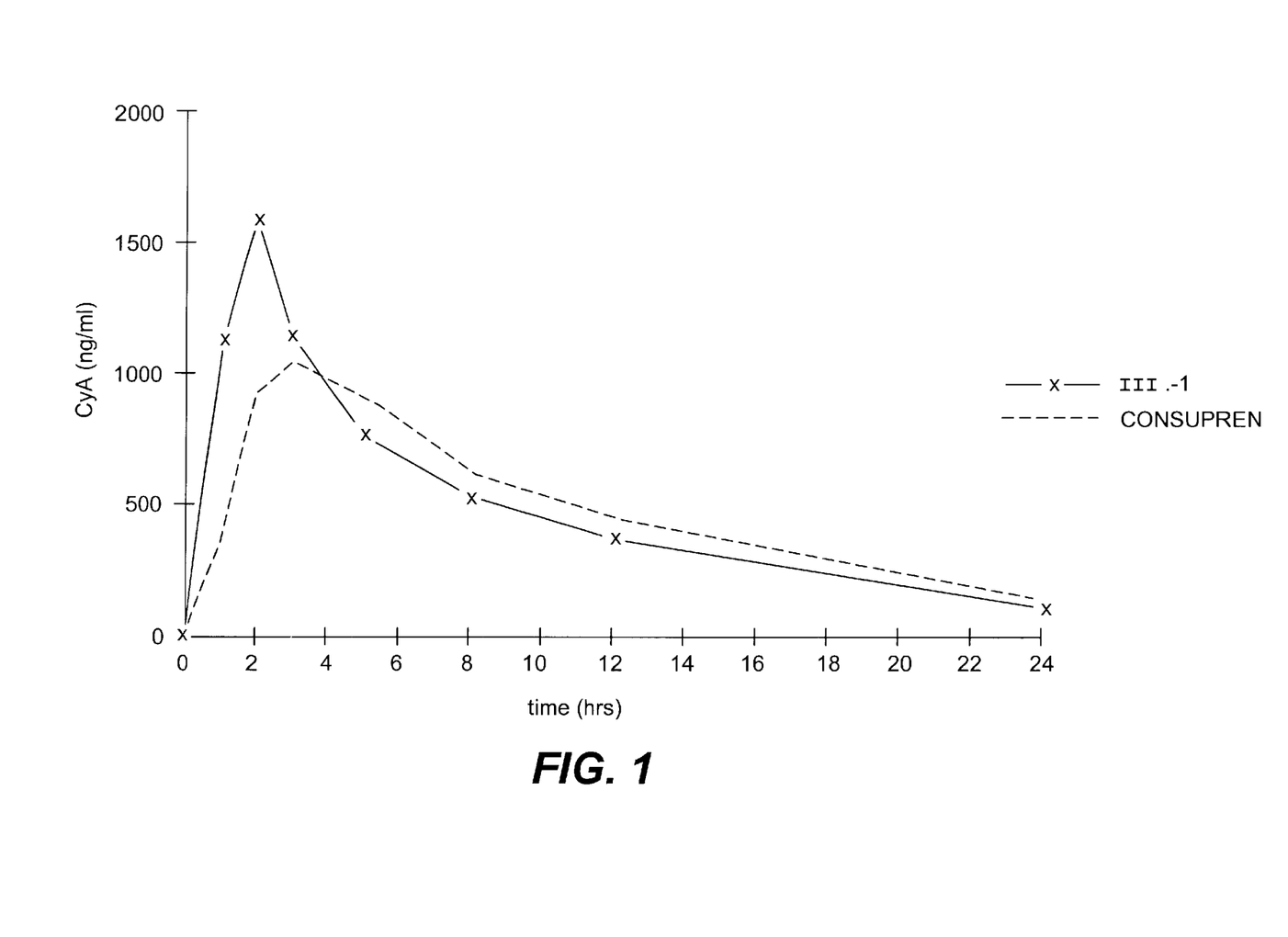
FIG. 1 is a graph comparing pharmacokinetic profiles of a product according to the invention with a comparative product.
Figure 2:
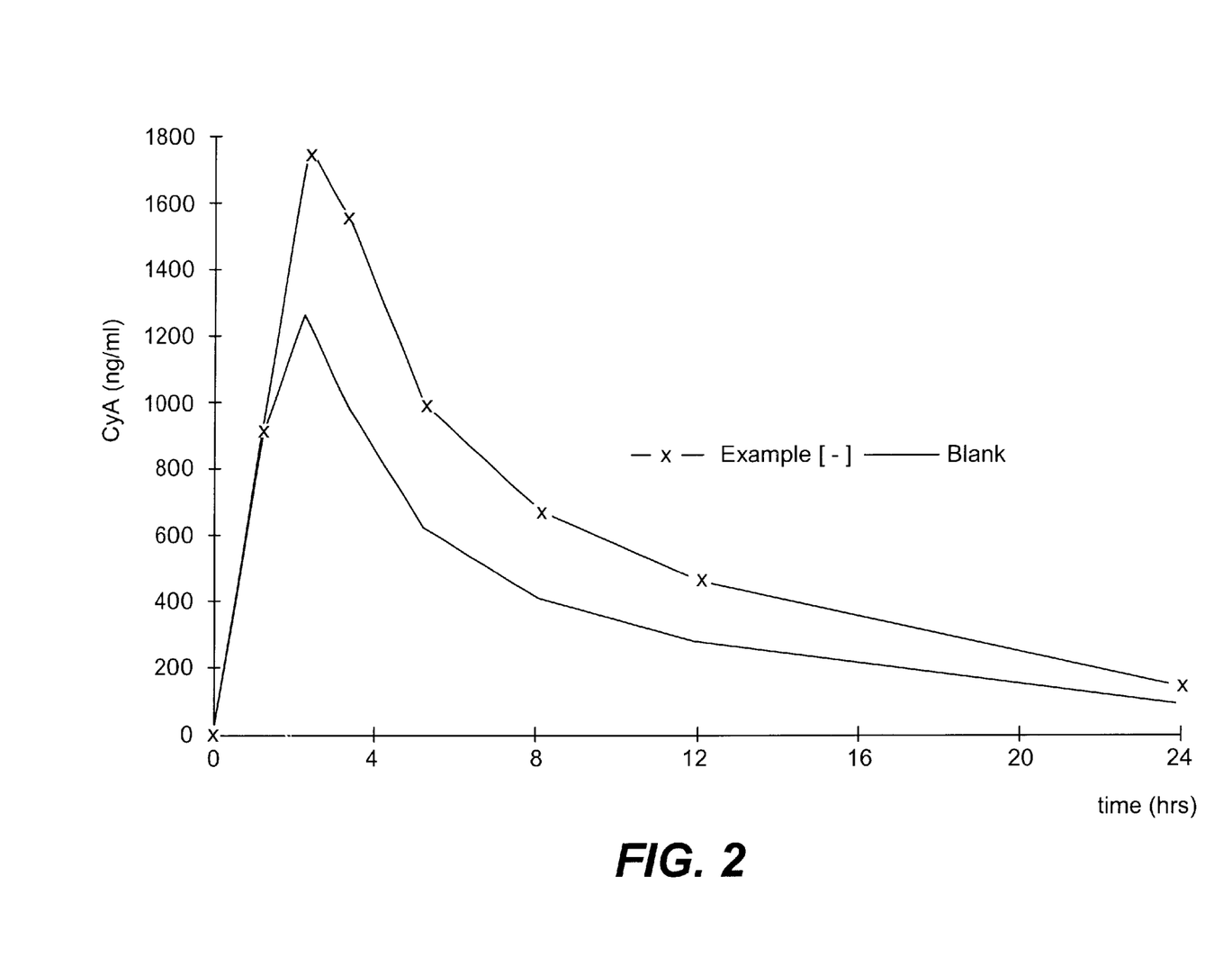
FIG. 2 shows a graph of cyclosporin blood level dependence on time for a formulation according to the invention and a comparative example.
Figure 3:
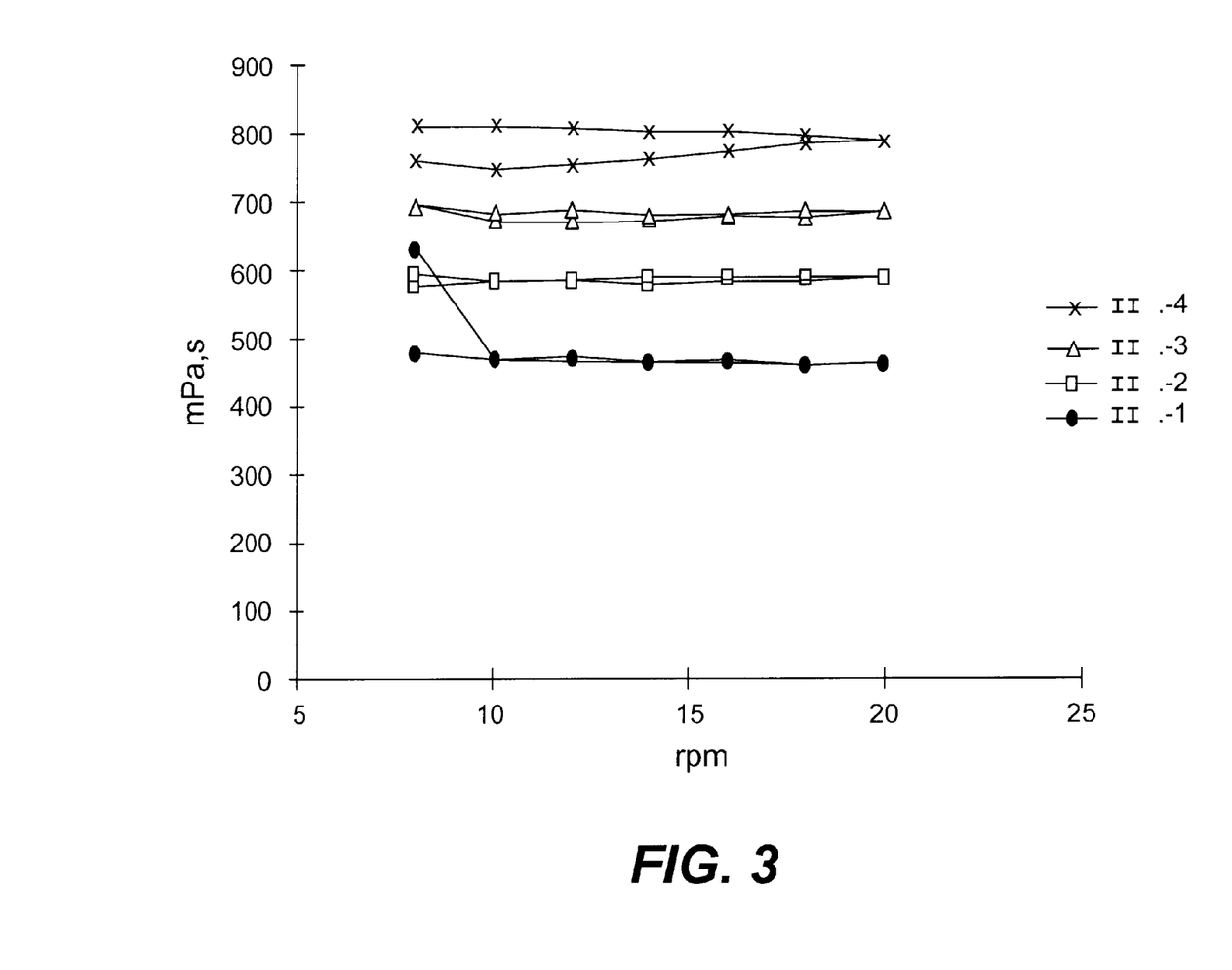
FIG. 3 is a graph of viscosity dependence on consurfactant.

FIG. 1 is a graph comparing pharmacokinetic profiles of a product according to the invention with a comparative product;

FIG. 2 shows a graph of cyclosporin blood level dependence on time for a formulation according to the invention and a comparative example;

FIG. 3 is a graph of viscosity dependence on cosurfactant; and

Figure 4:
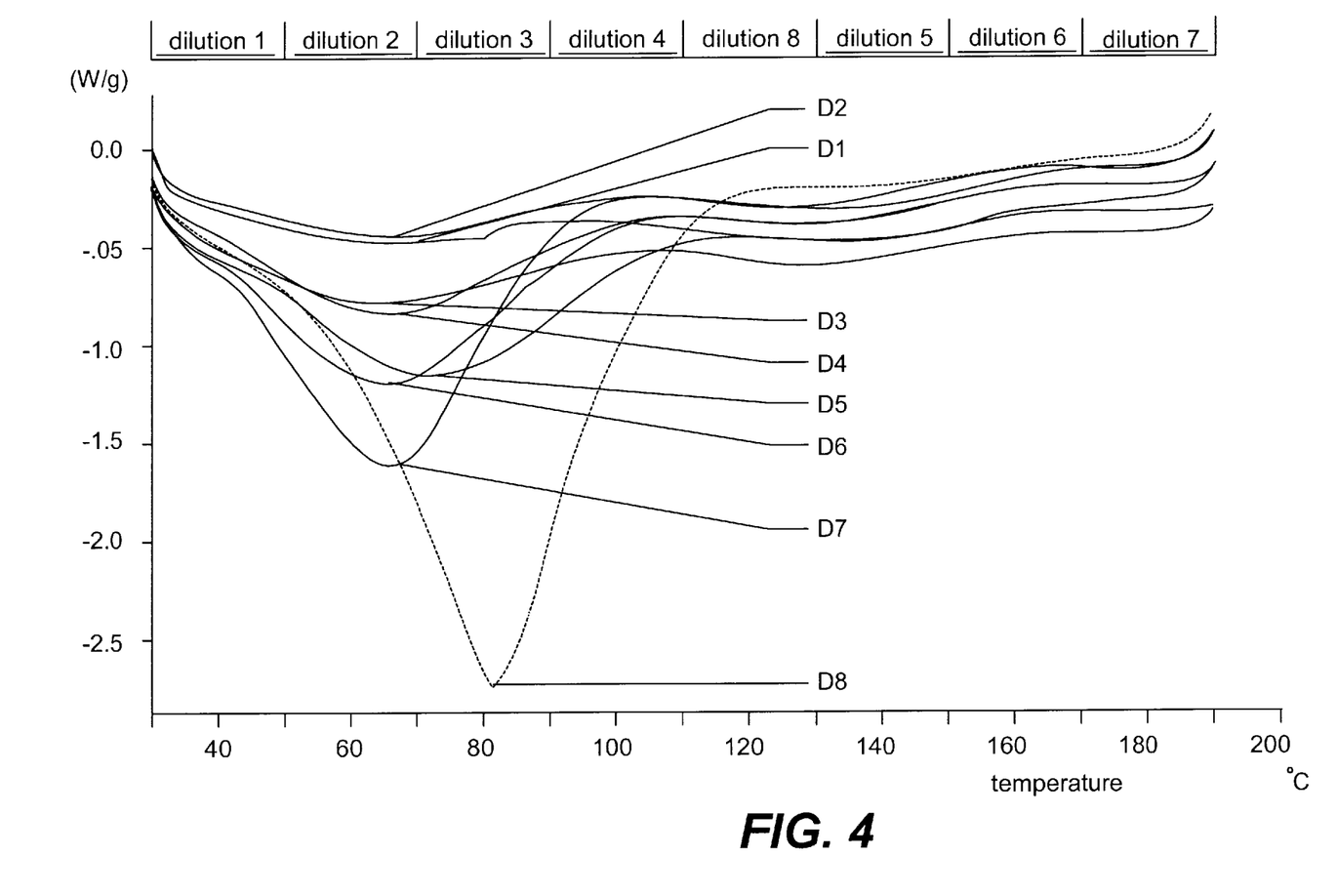
FIG. 4 is a graph showing specific heat absorptions after addition of water.

FIG. 4 is a graph showing specific heat absorptions after addition of water. after addition of water.

The following part summarises examples of various variants of composition of the pharmaceutical compositions.

EXAMPLE I-1

| A | cyclosporin | 50.0 mg |
|---|---|---|
| B | oleic acid | 157.5 mg |
| C1 | macrogol(1760)glycerol hydroxystearate | 225.0 mg |
| C3 | polysorbate | 67.5 mg |

EXAMPLE II-1

| A | cyclosporin | 10.0 g |
|---|---|---|
| B1 | oleic acid | 10.0 g |
| B2 | diglyceryl monoleate | 20.0 g |
| C1 | macrogol(1760)glycerol hydroxystearate | 40.0 g |
| C3 | Arlasolve ® DMI | 10.0 g |

EXAMPLE II-2

| A | cyclosporin | 10.0 g |
|---|---|---|
| B1 | oleic acid | 10.0 g |
| B2 | diglyceryl monooleate | 20.0 g |
| C1 | macrogol(1760)glycerol hydroxystearate | 40.0 g |
| C3 | propyleneglycol | 10.0 g |

EXAMPLE II-3

| | | |
|---|---|---|
| A | cyclosporin | 10.0 g |
| B1 | oleic acid | 10.0 g |
| B2 | diglyceryl monooleate | 20.0 g |
| C1 | macrogol(1760)glycerol hydroxystearate | 40.0 g |
| C3 | polyethylene glycol 400 | 10.0 g |

EXAMPLE II-4

| | | |
|---|---|---|
| A | cyclosporin | 10.0 g |
| B1 | oleic acid | 10.0 g |
| B2 | diglyceryl monooleate | 20.0 g |
| C1 | macrogol(1760)glycerol hydroxystearate | 40.0 g |
| C3 | Tween ® 20 | 10.0 g |

EXAMPLE III-1

| | | |
|---|---|---|
| A | cyclosporin | 50.0 mg |
| B1 | oleic acid | 50.0 mg |
| B2 | decaglyceryl monolaurate | 42.5 mg |
| C1 | macrogol(1760)glycerol hydroxystearate | 200.0 mg |
| C2 | oleyl alcohol | 105.0 mg |
| D | D-α-tocopherol | 2.5 mg |
| D | water | 50.0 mg |

EXAMPLE IV

| | | |
|---|---|---|
| A | cyclosporin | 0.60 kg |
| B3 | glyceryl monooleate | 0.81 kg |
| C1 | macrogol(4400)glycerol hydroxystearate | 2.76 kg |
| C2 | oleyl alcohol | 1.80 kg |
| D | D-α-tacopherol | 0.03 kg |

Example V

| | | |
|---|---|---|
| A | cyclosporin | 0.60 kg |
| B2 | diglyceryl monooleate | 0.57 kg |
| B2 | decaglyceryl monolaurate | 0.96 kg |
| C1 | macrogol(1760)glycerol hydroxystearate | 1.53 kg |
| C3 | propyleneglycol | 1.20 kg |

EXAMPLE VI

| | | |
|---|---|---|
| A | cyclosporin | 100.0 mg |
| B1 | Edenor ® SB 05 | 135.0 mg |
| C1 | Labrasol ® | 585.0 mg |
| C3 | Arlasolve ® DMI | 180.0 mg |

EXAMPLE VII

| | | |
|---|---|---|
| A | cyclosporin | 200.0 mg |
| B1 | linolenic acid | 250.0 mg |
| C1 | Synperonic ® L 64 | 550.0 mg |

EXAMPLE VIII

| | | |
|---|---|---|
| A | cyclosporin | 100.0 mg |
| B1 | linolenic acid | 200.0 mg |
| C1 | Pyroter ® CPI-40 | 700.0 mg |

EXAMPLE IX

| | | |
|---|---|---|
| A | rapamycine | 20.0 mg |
| B2 | decaglyceryl monooleate | 80.0 mg |
| B3 | glycerol monooleate | 50.0 mg |
| C1 | macrogol(1760)glycerol hydroxystearate | 200.0 mg |
| C2 | oleyl alcohol | 100.0 mg |
| C3 | propylene glycol | 50.0 mg |

EXAMPLE X

| | | |
|---|---|---|
| A | tacrolimus | 10.0 mg |
| B1 | oleic acid | 100.0 mg |
| C1 | macrogol(2200)glycerol hydroxystearate | 150.0 mg |
| C2 | oleyl alcohol | 150.0 mg |
| C3 | propylene glycol | 50.0 mg |
| D | D-tocopherol | |

General Method of Preparation

Component A was mixed together with components B1, C2 and C3. The mixture was allowed to dissolve at a maximum temperature of 40° C. with continuous mixing. The residual components B and C or D were added and the mixture was homogenized at an increased temperature. The resulting product was filtered if necessary. The intermediate product prepared in this way was ready for further handling and packing into bottles or containers for filling into both types of gelatin capsules, starch capsules, tubes or syringes or for preparation of other types of single unit dosage forms.

EXAMPLE XI

A role of an absorption promoter was verified by comparison of bioavailabilities. Formulation I-1 containing an absorption promoter was compared with a formulation without absorption promoter indicated as "Blank" in the text. As B1 and C2 have the same effect from a technical point of view (they dissolve the active ingredient well) component B1 was replaced by component C2 in the "Blank" composition.

Composition of the comparative sample indicated as "Blank" is as follows:

| A  | ciclosporin                            | 50.0 mg  |
|----|----------------------------------------|----------|
| C2 | oleyl alcohol                          | 157.5 mg |
| C1 | macrogol(1760)glycerol hydroxystearate | 225.0 mg |
| C3 | polysorbate                            | 67.5 mg  |

Pharmacokinetic comparison was carried out after administration of a single dose of 100 mg cyclosporin in two-phase experiment in 10 Beagle dogs. Males aged between 12–36 months of weight 9–15 kg were used. The dogs were fed with a standard pellet diet in quantity 300 g per day with water ad libitum.

The product was administered after 18 hour fasting period. Blood collections were taken from foreleg vein in 0, 1, 2, 3, 51 8, 12, 24 hour intervals. Blood samples were stabilised by complexone and immediately frozen for determination by non-specific radioimmunoassay. The bioavailability comparison of both formulations is summarised in FIG. 2. Substantially higher bioavailability of the formulation with absorption promoter was apparent.

EXAMPLE XII

An influence of component C3 on viscosity of a resulting mesophase was evaluated. A constant quantity of water was added to standard formulations prepared according to Examples II-1 to II-4. Rheological properties were evaluated.

Method of Preparation

Component A was mixed with components B1, B2 and C3 and dissolved under intensive mixing at temperature to 40° C. Component C1 was added and the mixing continued until the mixture was clear. The resulting solution was filtered under overpressure about 0.2–0.5 MPa $N_2$ through a membrane filter of type GVHP 0.22 µm (Millipore). As cosurfactant, Arlasolve DMI, propyleneglycol, polyethyleneglycol 400 and polysorbate 20 were used.

Water for injections in ratio 3:1 (preconcentrate:water) was added to the preconcentrates. The resulting gel like mesophase were properly homogenized.

The rheological properties of the systems prepared this way were evaluated on a rotary viscosimeter Brookfield DV-III under constant conditions, temperature=20° C., spindle SC 4-21, ultrathermostat Brookfield TC 500, evaluation on PC (Rheocalc program, 1.3 version)

The graph in FIG. 3 illustrates the possibility of change of rheological parameters in situ resulting phase by suitable selection of component C3. It also shows that a certain amount of water added to the preconcentrate at needed time to dramatically change the rheological properties and enable its use for topical application.

EXAMPLE XIII

Bioavailability of formulation III-1 was compared with a commonly commercially available product Consuprene oral solution. Formulation III-1 was prepared as follows: Ciclosporin was dissolved in a mixture of oleic acid and oleyl alcohol under temperature to 40° C. At the same time, decaglyceryl monolaurate, macrogol(1760) glycerol hydroxystearate and D-α-tocopherol were mixed under increased temperature (approx 50° C.). Both parts, properly homogenized and at the same temperature were mixed, filtered under overpressure through a membrane filter 0,22 µm and purified water added. The product obtained in a form of lyotropic crystals was filled in amount 500 mg per capsul into hard gelatin capsules of size "0".

Pharmacokinetic comparison was carried out after administration of a single dose of 100 mg cyclosporin in a two-phase experiment in 10 Beagle dogs. Males aged between 12–36 months of weight 9–15 kg used. The dogs were fed with a standard pellet diet in quantity 300 g per day with water ad libitum.

The product was administered after 18 hour fasting period. Blood collections were taken from foreleg vein in 0, 1, 2, 3, 5, 8, 12, 24 hour intervals. Blood samples were stabilised by complexone and immediately frozen until determination by non-specific radioimmunoassay.

Comparison of pharmacokinetic profiles of formulation III and a standard product Consupren® oral solution is summarised in FIG. 1 and indicates that the bioavailability of composition according to this invention is higher than that of standard product Consupreno oral solution.

EXAMPLE XIV

Differential scanning calorimetry was used for characterisation and classification changes occurring during dilution. The following formulation was prepared.

| A  | cyclosporine                         | 0.0829 mol |
|----|--------------------------------------|------------|
| B2 | diglyceryl monooleate                | 0.2787 mol |
| B2 | decaglyceryl monolaurate             | 0.1961 mol |
| C1 | macrogol (1760) glycerolhydroxystearate | 0.1038 mol |
| C2 | oleyl alcohol                        | 0.7076 mol |
| C3 | propylene glycol                     | 1.5789 mol |

The prepared sample was diluted with water n the below mentioned molar fractions to form liquid crystalline structures. The diluted samples were tested by differential scanning calorimetry on a Mettler DSC 12E apparatus under constant conditions (temperature range: 30–200° C.; temperature step: 10° C./min). Results were evaluated by Metier TA89E software and are listed in the table below.

According to the DSC results the system became stable with high water content and required more energy for melting.

| $X_{i(water)}$ | $t_1$ (° C.) | $t_2$ (° C.) | $\Delta H_1$ (J/g) | $\Delta H_2$ (J/g) |
|---------|-------|-------|-----|----|
| 0.312   | 68.3  | 139.4 | 79  | 39 |
| 0.680   | 66.5  | 138.1 | 95  | 33 |
| 0.796   | 65.5  | 136.2 | 140 | 24 |
| 0.852   | 67.8  | 136.7 | 158 | 27 |
| 0.908   | 73.1  | 147.6 | 277 | 18 |
| 0.923   | 65.7  | 135.9 | 248 | 16 |
| 0.944   | 67.0  | 135.0 | 312 | 20 |
| 0.966   | 82.8  | 150.5 | 581 | 7  |

$X_{i(water)}$-molar fraction of water
$t_1$-transient temperature (° C.)
$t_2$-transient temperature (° C.)
$\Delta H_1$-1 molar absorbtion heat (J/g)
$\Delta H_2$-2 molar absorbtion heat (J/g)

What we claim is:

1. An immunomodulatory pharmaceutical composition adopted to form lyotropic liquid crystals in contact with an aqueous phase comprising:

A 1 to 35% by weight of an active ingredient selected from: N-methylated cyclic undecapeptides or macrolide lactones; and a carrier medium comprising:

B 1 to 40% by weight of at least one absorption promoter;

C a non-lipidic vehicle containing at least one of:

C1 1 to 80% by weight of a surfactant or mixtures of surfactant with HLB greater than 9;
C2 1 to 30% by weight of a lipophilic solvent comprising one or more higher fatly alcohols; and
C3 1 to 50% by weight of at least one of the following:
a polyether of general formula $H\text{—}[O\text{—}CH_2\text{—}CH_2\text{—}]_n\text{—}OH$, where n is an integer from 1 to 20;
a cyclic polyether of general formula where R is $C_{1-3}$ alkyl;
one or more polyols having 3 carbon atoms and/or their mono- to poly-esters with sorbians of fatty acids, macrogolsorbitans of fatty acids, polyoxyethylated fatty acids or mono- to poly-esters of fatty acids;
wherein the ratio of components A:B:C is 1:0.1–20:0.5–35 by weight and wherein the aforementioned amounts of ingredients total 100%.

2. A composition as claimed in claim 1, wherein the ratio of components A:B:C is 1:0.5–4:5–8.

3. A composition as claimed in claim 1, wherein the active ingredient is selected from the group comprising: cyclosporin, [Nva]²-cyclosporin, [MeIle]⁴-cyclosporin and [3-O-acyl MeBmt]¹.

4. A composition as claimed in claim 1, wherein the active ingredient is rapamycine, tacrolimus or a derivative thereof.

5. A composition as claimed in claim 1, wherein component B comprises one or more of:
B1 saturated or unsaturated $C_{8-22}$ fatty acids or mixtures thereof;
B2 polyglycerol esters of fatty acids of general formula wherein n is an integer from 0 to 14 and R=H or a $C_{8-22}$ acyl derivative from saturatated and/or unsaturated fatty acids and/or hydroxylated fatty acids or mixtures thereof;
B3 glycerol monoesters with fatty acids or mixtures thereof,
wherein the ratio of B:A is 0.5:1 to 6:1.

6. A composition as claimed in claim 1, wherein component C2 comprises one or more $C_{12-22}$ unsaturated fatty alcohols.

7. A composition as claimed in claim 6, including a combination of components C1 and C2 in a ratio C1:C2 of 4.5:1 to 0.1:1.

8. A composition as claimed in claim 1, wherein the amount of component C3 is 5–30% by weight.

9. A pharmaceutical composition of claim 1, further including a component D to Provide stability against microbial oxidative processes or to change the product into a lyotropic crystalline form during preparation.

10. A composition as claimed in claim 9, wherein the ratio of components D:(A+B+C) is 0.01–10:1.

11. A composition as claimed in claim 1, characterised that in contact with a hydrophilic phase, the composition forms a non-birefringent gel phase.

12. A composition as claimed in claim 9, wherein the ratio of components D:(A+B+C) is 0.1–6:1.

* * * * *